United States Patent [19]
Hansen et al.

[11] 3,956,388
[45] May 11, 1976

[54] N-METHYLOL ETHERS OF GLYCOLLIC ANILIDES

[75] Inventors: Hanspeter Hansen, Ludwigshafen; Wolfgang Rohr, Mannheim, both of Germany

[73] Assignee: BASF Aktiengesellschaft, Ludwigshafen (Rhine), Germany

[22] Filed: Mar. 20, 1975

[21] Appl. No.: 560,312

[52] U.S. Cl............................ 260/562 R; 260/562 A
[51] Int. Cl.²........................................ C07C 103/38
[58] Field of Search...................... 260/562 R, 562 A

[56] References Cited
UNITED STATES PATENTS 3,646,141   2/1972   Randall........................... 260/562 B

*Primary Examiner*—C. Davis
*Attorney, Agent, or Firm*—Johnston, Keil, Thompson & Shurtleff

[57] ABSTRACT

New and valuable glycollic anilide N-methylol ethers and methods of producing the same.

7 Claims, No Drawings

N-METHYLOL ETHERS OF GLYCOLLIC ANILIDES

This application discloses and claims subject matter described in German Pat. application No. P 24 17 781.9, filed Apr. 11, 1974, which is incorporated herein by reference.

The invention relates to new glycollic anilide N-methylol ethers of the general formula:

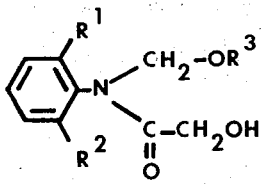

in which
at least one of the radicals $R^1$ and $R^2$ is alkyl or alkoxy of one to four carbon atoms or halogen and
$R^3$ is a substituted or unsubstituted alkyl, alkenyl or alkynyl of one to four carbon atoms.

The radicals $R^1$ and $R^2$ may be identical or different; when only one of the two radicals has one of the above meanings, the other radical is hydrogen.

The compounds are directly suitable as precursors for the production of herbicides. Compounds of the abovementioned type in which the hydroxyl groups of the glycollic acid radical are replaced for example by a sulfamoyl group are effective herbicides. Substitution by halogen at the same place also gives herbicides.

The invention is to be seen against the background of German Laid-Open Specifications (DOS) Nos. 2,226,593 and 1,542,950, in which compounds of a similar type are described which have also proved to be suitable as herbicides. Among other prior references, compounds are also disclosed in U.S. Pat. Nos. 3,630,716 and 3,637,847 which have a certain relationship to the new compounds of the invention.

The new compounds may be obtained in the following way: one possibility for example is the reaction of an o-toluidine or o,o'-xylidine (or their analogous allied substances having other radicals $R^1$ and/or $R^2$ instead of methyl groups) into an azomethine (this is described for example in German Laid-Open Specification (DOS) 1,542,950) and the conversion of the azomethine (Schiff's base) with acetylglycollyl chloride into the corresponding nuclear substituted N-(chloromethyl)-2-acetoxyacetanilide (for example in an inert solvent such as hexane, benzene or toluene at a temperature of from about 5° to 70°C and preferably at ambient temperature or slightly elevated temperature) and hydrolysis with a suitable alkali metal alcoholate. This is illustrated by the following equation (1):

Another method, which also gives the new substances in good yields, consists in reacting a chloroacetyl derivative of the aniline N-methylol ether concerned with sodium acetate followed by hydrolysis according to the following steps:

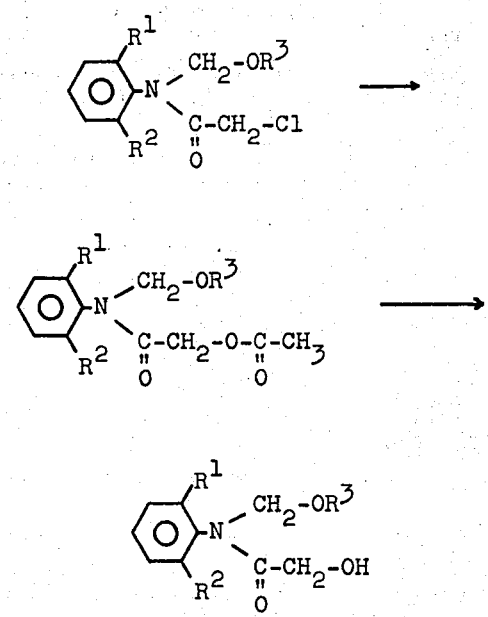

The following details are given concerning the compounds according to the invention:

Examples of lower alkyl or alkoxy radicals $R^1$ and/or $R^2$ are methyl, ethyl, n-propyl, isopropyl, n-butyl, isobutyl, sec.-butyl, tert.-butyl, methoxy, ethoxy, n-propoxy, isopropoxy, n-butoxy, isobutoxy, n-propyloxy, isopropyloxy, n-butyloxy and isobutyloxy and also halogen, i.e. fluoro, chloro, bromo and iodo.

Radical $R^3$ may according to the invention be linear or branched alkyl of one to four carbon atoms such as are listed above for $R^1$ and/or $R^2$; if desired this radical may bear a halogen atom, alkoxy group or cyano group once or more than once as a substituent; it may also have olefinic or acetylenic unsaturation.

Examples of the last mentioned radicals are allyl, 2-methallyl, dichloroallyl, trichloroallyl and butyn-1-yl-3. Thus, $R^3$ also may be alkenyl, haloalkenyl or alkynyl of one to four carbon atoms.

Examples of new substances which can be obtained as described above and which have the above formula are:

2',6'-dimethyl-N-(methoxymethyl)-2-hydroxyacetanilide,

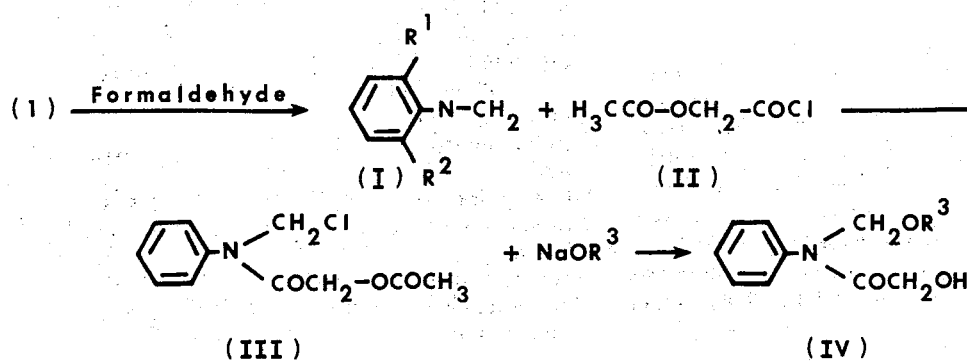

2',6'-dimethyl-N-(ethoxymethyl)-2-hydroxyacetanilide,
2',6'-dimethyl-N-(isopropoxymethyl)-2-hydroxyacetanilide,
2',6'-dimethyl-N-(butoxymethyl)-2-hydroxyacetanilide,
2',6'-diethyl-N-(methoxymethyl)-2-hydroxyacetanilide,
2',6'-diethyl-N-(ethoxymethyl)-2-hydroxyacetanilide,
2',6'-diethyl-N-(isopropoxymethyl)-2-hydroxyacetanilide,
2',6'-diethyl-N-(butoxymethyl)-2-hydroxyacetanilide,
2'-tert.butyl-6'-methyl-N-(methoxymethyl)-2-hydroxyacetanilide,
2'-tert.-butyl-6'-methyl-N-(ethoxymethyl)-2-hydroxyacetanilide,
2'-tert.-butyl-6'-methyl-N-(isopropoxymethyl)-2-hydroxyacetanilide,
2'-tert.butyl-6'-methyl-N-(butoxymethyl)-2-hydroxyacetanilide,
2',6'-diisopropyl-N-(methoxymethyl)-2-hydroxyacetanilide,
2',6'-diisopropyl-N-(ethoxymethyl)-2-hydroxyacetanilide,
2',6'-diisopropyl-N-(isopropoxymethyl)-2-hydroxyacetanilide and
2',6'-diisopropyl-N-(butoxymethyl)-2-hydroxyacetanilide.

The following Example illustrates the invention.

EXAMPLE a. 16.1 parts of 2,6-diethylphenylazomethine is dissolved in 30 parts of benzene, and 13.7 parts of acetylglycollyl chloride dissolved in 20 parts of benzene is added at 25° to 30°C. The reaction is over as soon as the exothermic reaction subsides. The whole is stirred for another fifteen minutes, the benzene is removed in vacuo and the crystalline substance obtained is washed with petroleum ether. 29 parts of the desired product is obtained. The compound has the following sturcture:

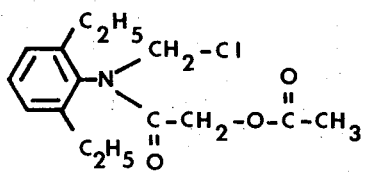

and a melting point of 56° to 57°C.

The following substances are obtained analogously: 2',6'-dimethyl-N-(chloromethyl)-2-acetoxyacetanilide having a melting point of 78° to 79°C, 2',6'-diisopropyl-N-(chloromethyl)-2-acetoxyacetanilide and 2'-methyl-6'-tert.-butyl-N-(chloromethyl)-2-acetoxyacetanilide.

For further reaction the chloromethyl compounds are dissolved in the alcohol whose alkoxy radical is to be introduced in place of the halogen atom and twice the molar amount of the corresponding alkali metal alcoholate is added.

b. 2',6'-diethyl-N-(methoxymethyl)-2-hydroxyacetanilide:

29.8 parts of 2',6'-diethyl-N-(chloromethyl)-2-acetoxyacetanilide is dissolved in 150 parts of methanol and at about 30°C has 11 parts of sodium methylate dissolved in 40 parts of methanol added to it dropwise. After about thirty minutes 20 parts of water is added and the solvent is removed in vacuo.

The residue which remains is digested with benzene. After the benzene has been removed there remains 20 parts of 2',6'-diethyl-N-(methoxymethyl)-2-hydroxyacetanilide:

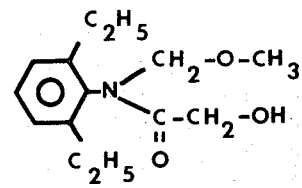

It has a boiling point of from 123° to 126°C at 0.01 mm; $n_{25} = 1.5244$.

The following compounds are obtained by a method analogous to that described in the Example:
2',6'-diethyl-N-(ethoxymethyl)-2-hydroxyacetanilide
boiling point: 136° to 141°C at 0.01 mm; $n_{25} = 1.5176$;
2',6'-diethyl-N-(isopropoxymethyl)-2-hydroxyacetanilide
boiling point: 134°C at 0.01 mm; $n_{25} = 1.5146$;
2',6'-diethyl-N-(n-butoxymethyl)-2-hydroxyacetanilide
boiling point: 154°C at 0.01 mm; $n_{25} = 1.5112$;
2',6'-dimethyl-N-(methoxymethyl)-2-hydroxyacetanilide;
melting point: 59° to 60°C; boiling point: 119° to 125°C at 0.01 mm;
2',6'-dimethyl-N-(ethoxymethyl)-2-hydroxyacetanilide;
boiling point: 121°C at 0.05 mm; $n_{25} = 1.5247$;
2',6'-dimethyl-N-(isopropoxymethyl)-2-hydroxyacetanilide;
boiling point: 123° to 125°C at 0.1 mm; $n_{25} = 1.5172$;
2',6'-dimethyl-N-(n-butoxymethyl)-2-hydroxyacetanilide:
boiling point: 135° to 141°C at 0.05 mm; $n_{25} = 1.5152$;
2',6'-dimethyl-N-(β-trifluoroethoxymethyl)-2-hydroxyacetanilide;
melting point: 46° to 48°C;
2',6'-dimethyl-N-(isobutoxymethyl)-2-hydroxyacetanilide;
boiling point: 139° to 142°C at 0.25 mm;
2',6'-dimethyl-N-(sec.butoxymethyl)-2-hydroxyacetanilide; boiling point: 160° to 165°C at 1 mm;
2',6'-diethyl-N-(propargoxymethyl)-2-hydroxyacetanilide;
boiling point: 150°C at 0.05 mm; $n_D^{19} = 1.5358$;
2',6'-dimethyl-N-(alloxymethyl)-2-hydroxyacetanilide; boiling point: 133° to 135°C at 0.1 mm; $n_D^{20} = 1.5351$;
2',6'-dimethyl-N-(propargoxymethyl)-2-hydroxyacetanilide;

boiling point: 143° to 146°C at 0.1 mm; $n_D^{24} = 1.5422$;
2',6'-diisopropyl-N-(methoxymethyl)-2-hydroxyacetanilide;
melting point: 125° to 127°C;
2'-tert.-butyl-6'-isopropyl-N-(methoxymethyl)-2-hydroxyacetanilide;
melting point: 125° to 127°C;
2'-ethyl-6'-methyl-N-(ethoxymethyl)-2-hydroxyacetanilide; boiling
point: 145° to 149°C at 1 mm; $n_D^{25} = 1.5210$.

We claim:
1. A glycollic anilide-N-methylol ether of the general formula:

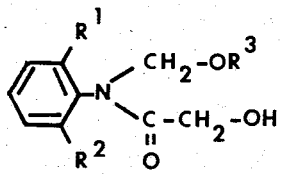

in which
at least one of the radicals $R^1$ and $R^2$ is alkyl or alkoxy of one to four carbon atoms or halogen, one optionally being hydrogen, and $R^3$ is halo-, alkoxy- or cyano- substituted or unsubstituted alkyl, alkenyl, haloalkenyl or alkynyl of one to four carbon atoms.

2. A process for the production of a glycollic anilide-N-methylol ether of the general formula:

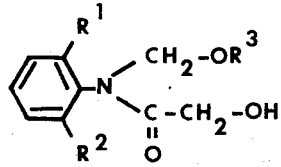

in which
at least one of the radicals $R^1$ and $R^2$ is alkyl or alkoxy of one to four carbon atoms or halogen and $R^3$ is halo-, alkoxy- or cyano- substituted or unsubstituted alkyl, alkenyl, haloalkenyl or alkynyl of one to four carbon atoms wherein an azomethine of the formula:

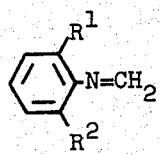

in which $R^1$ and $R^2$ have the meanings given above is reacted with acetylglycollyl chloride to give an N-(chloromethyl)-2-acetoxyacetaniline of the formula

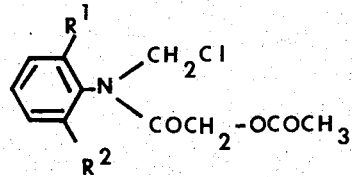

in which $R^1$ and $R^2$ have the above meanings and this compound is hydrolyzed with an alkali metal alcoholate of the formula MeOR$^3$ in which Me is an alkali metal and $R^3$ has the above meanings.

3. An ether as claimed in claim 1 wherein $R^1$ and $R^2$ each denote alkyl of 1–4 carbon atoms and $R^3$ denotes alkyl of 1 to 4 carbon atoms.

4. An ether as claimed in claim 1 wherein $R^1$ and $R^2$ each denote methyl and $R^3$ denotes alkyl of 1 to 4 carbon atoms.

5. An ether as claimed in claim 1 wherein $R^1$ And $R^2$ each denote ethyl and $R^3$ denotes alkyl of 1 to 4 carbon atoms.

6. An ether as claimed in claim 1 wherein $R^1$ and $R^2$ each denote alkyl of 1–4 carbon atoms and $R^3$ denotes alkenyl having 2-4 carbon atoms, dichloroallyl or trichloroallyl.

7. An ether as claimed in claim 1 wherein $R^1$ and $R^2$ each denote alkyl of 1–4 carbon atoms and $R^3$ denotes alkynyl having 2-4 carbon atoms.

* * * * *

UNITED STATES PATENT AND TRADEMARK OFFICE
CERTIFICATE OF CORRECTION

PATENT NO. : 3,956,388
DATED : May 11, 1976
INVENTOR(S) : HANSEN et al

It is certified that error appears in the above-identified patent and that said Letters Patent are hereby corrected as shown below:

In the Heading, insert -- [30] Foreign Application Priority Data   April 11, 1974   Germany   P 24 17 781.9 --

Signed and Sealed this

Second Day of November 1976

[SEAL]

Attest:

RUTH C. MASON
Attesting Officer

C. MARSHALL DANN
Commissioner of Patents and Trademarks